United States Patent
Dominiani, Jr. et al.

(10) Patent No.: US 8,133,846 B2
(45) Date of Patent: Mar. 13, 2012

(54) STABLE DISPERSIONS OF SULFENTRAZONE IN A CONTINUOUS PHASE OF AQUEOUS GLYPHOSATE SALT

(75) Inventors: Frank J. Dominiani, Jr., Flemington, NJ (US); Timothy Martin, Ringoes, NJ (US); Janie L. Zitomer, East Brunswick, NJ (US)

(73) Assignee: FMC Corporation, Philadelphia, PA (US)

( * ) Notice: Subject to any disclaimer, the term of this patent is extended or adjusted under 35 U.S.C. 154(b) by 276 days.

(21) Appl. No.: 12/370,305

(22) Filed: Feb. 12, 2009

(65) Prior Publication Data

US 2009/0209424 A1    Aug. 20, 2009

Related U.S. Application Data

(60) Provisional application No. 61/028,661, filed on Feb. 14, 2008.

(51) Int. Cl.
*A01N 57/00* (2006.01)
(52) U.S. Cl. .................................................. 504/127
(58) Field of Classification Search .................. None
See application file for complete search history.

(56) References Cited

U.S. PATENT DOCUMENTS

| | | | | |
|---|---|---|---|---|
| 6,127,318 A | * | 10/2000 | Sato et al. | 504/128 |
| 6,713,433 B2 | | 3/2004 | Jimoh | |
| 2005/0221985 A1 | * | 10/2005 | Garcia et al. | 504/128 |

* cited by examiner

*Primary Examiner* — Johann Richter
*Assistant Examiner* — Thor Nielsen
(74) *Attorney, Agent, or Firm* — FMC Corporation

(57) ABSTRACT

The present invention is directed to novel suspension concentrate compositions comprising finely milled crystalline sulfentrazone suspended in an aqueous glyphosate salt phase containing a surfactant component that chemically and physically stabilizes the composition.

10 Claims, No Drawings

STABLE DISPERSIONS OF SULFENTRAZONE IN A CONTINUOUS PHASE OF AQUEOUS GLYPHOSATE SALT

FIELD OF THE INVENTION

The present invention relates to the field of agrochemical suspension concentrate compositions.

BACKGROUND OF THE INVENTION

To enable the efficient elimination or controlling of unwanted plants, it is desirable to use effective chemical formulations of herbicides. Compositions containing two or more herbicides are desirable in agricultural, specialty applications and related endeavors due to broadening the spectrum or range of unwanted plant species killed or controlled.

Due to the desirability of having a composition with the above-mentioned properties, it is useful to use combinations of herbicides to obtain enhanced control of numerous weeds with a single application. Combinations of pesticides are known and available as mixed solutions of the active ingredients in their commercially available formulations. One method of preparing such a composition is referred to as "tank mixing" in which the ingredients in their commercially available form are mixed together by the user in a quantity of water. Tank mixes require the end user to purchase two or more commercial formulations, store them, calculate the correct amount of each active ingredient, measure those amounts into the mix and when empty, properly dispose of a number of containers. Combining the active ingredients into one formulation is beneficial but frequently more complex due to widely different physical properties of the active ingredients in which chemical and physical stability are problems.

Sulfentrazone, the common name for N-[2,4-dichloro-5-[4-(difluoromethyl)-4,5-dihydro-3-methyl-5-oxo-1H-1,2,4-triazol-1-yl]phenyl]methanesulfonamide, a highly effective post-emergence herbicide, chemically degrades in the presence of water. Glyphosate, the common name for N-(phosphonomethyl)glycine, is a most effective pre and post-emergence herbicide especially when applied as a salt of glyphosate, for example, the isopropylamine salt. Glyphosate salts are water-soluble and are normally formulated in an aqueous medium.

Co-formulations containing sulfentrazone and a glyphosate salt are known. For example, U.S. Pat. No. 6,713,433 discloses an oil-in-water microemulsion of sulfentrazone, using volatile organic solvents to solubilize the sulfentrazone prior to emulsification, in an aqueous glyphosate salt phase. U.S. Pat. No. 6,127,318 discloses emulsion formulations and an emulsifiable concentrate formulation of a triazolinone herbicide and glyphosate salt in which volatile aromatic solvents are used to solubilize the triazolinone herbicide.

The use of volatile organic and aromatic solvents in herbicide formulations which are to be sprayed onto crops, turf sites and the like are being discouraged by environmental agencies because of health, safety and environmental impact concerns. It would be most beneficial to eliminate volatile organic and aromatic solvents from herbicidal formulations while maintaining a stable, non-degrading liquid formulation.

SUMMARY OF THE INVENTION

The present invention provides a novel herbicidal suspension concentrate composition of sulfentrazone in a continuous phase of aqueous glyphosate salt that has superior chemical and physical stability.

Specifically, the present invention is directed to a novel suspension concentrate composition comprising finely milled crystalline sulfentrazone suspended in an aqueous glyphosate salt phase, containing a surfactant component that chemically and physically stabilizes the composition. The present suspension concentrate contains no volatile organic compounds that would impact health, safety or the environment.

DETAILED DESCRIPTION OF THE INVENTION

The present invention relates to a novel suspension concentrate composition comprising finely milled crystalline sulfentrazone suspended in an aqueous glyphosate salt phase containing a surfactant component. In particular the suspension concentrate composition of the present invention comprises:

i) crystalline sulfentrazone;
ii) an aqueous glyphosate salt phase; and
iii) a surfactant component comprising:
   an amine salt of alkylbenzenesulfonic acid,
   a methyl oleoyl taurate salt, and
   an alkyl polyglycoside.

The suspension concentrate composition may further comprise one or more of an antifoam agent, an antifreeze agent, a preservative, water and a thickener or suspending agent. In particular, the novel suspension concentrate composition comprises finely milled crystalline sulfentrazone suspended in an aqueous glyphosate salt phase to which is added a unique surfactant component comprising an amine salt of alkylbenzenesulfonic acid, a methyl oleoyl taurate salt and an alkyl polyglycoside.

A suspension concentrate (SC) is a formulation in which a solid active ingredient(s) is suspended in a liquid carrier, intended for dilution with water before use.

In the present invention, crystalline sulfentrazone is milled to a small particle size in order to prevent clogging spray nozzles. The preferred particle size is about 10 microns or less, achieved by milling an aqueous mixture containing sulfentrazone in, for example, a bead or ball mill. One or more additional components selected from an aqueous glyphosate salt solution, surfactants, an antifoam agent, an antifreeze agent, a preservative and a thickener or suspending agent can be added to the aqueous mixture prior to milling, or the additional components can be added after the milling process has taken place.

The ratio of sulfentrazone to glyphosate salt can vary over a wide range but is usually in the range of 1:5 to 1:99, preferably 1:5 to 1:20 and most preferably is a ratio of about 1:7. Sulfentrazone is present in an amount from 3% to 10% by weight, preferably in an amount of from 5% to 7% by weight of all the components in the total composition. The glyphosate salt is preferably the isopropylammonium salt of glyphosate (glyphosate IPA) and is present in an amount of from 30% to 50% by weight, preferably in an amount of from 40% to 50% by weight of all the components in the total formulation.

The surfactant component of the present invention is comprised of at least three surfactants; an amine salt of alkylbenzenesulfonic acid, a methyl oleoyl taurate salt and an alkyl polyglycoside. The amine salt of alkylbenzenesulfonic acid is preferably the isopropylamine salt of alkylbenzenesulfonic acid (C9-17 Br), for example, NINATE° 411, available form Stepan Mexico, S. A. de C. V. and is present in an amount of from 0.5% to 2% by weight, more preferably in an amount of from 0.7% to 1% by weight of all the components in the total composition. The methyl oleoyl taurate salt is preferably sodium methyl oleoyl taurate, for example, GEROPON® T-77, available form Rhodia Inc. and is present in amount of from 2% to 4% by weight, more preferably 2.7% to 3.0% by weight of all the components in the total composition. The alkyl polyglycoside is preferably the alkyl poylglycoside surfactant AGNIQUE® PG 8105 available from Cognis Corporation and is present in an amount of from 0.5% to 2% by weight, more preferably 0.8% to 1% by weight of all of the components in the total composition.

The composition can further comprise an anti-foam agent; a thickening agent; an antifreeze agent and an anti-microbial agent (biocide). Preferably, the anti-foam agent is a silicone emulsion, for example, DOW CORNING® AF Emulsion available from Dow Corning Corporation, present in an amount of from 0.001% by weight to 0.5% by weight of all components in the total composition. Preferably, the thickening agent is xanthan gum, for example, RHODOPOL 23 brand of xanthan gum, available from Rhone-Poulenc, Inc. or KELZAN® S, available from CP Kelco A Huber Company, present in an amount of from 0.02% by weight to 0.25% by weight of all components in the total composition. Preferably the antifreeze agent is a glycol, for example, propylene glycol, present in an amount of from 1% to 10% by weight of all the components in the total composition. Preferably the anti-microbial agent is KATHON™ GC/ICP or LEGEND® MK both available from Rohm and Haas Corporation, and is present in an amount of from 0.001% by weight to 0.5% by weight of all components in the total composition.

A particular embodiment of the present invention is a method for the control of unwanted plants comprising applying a pesticidally effective amount of the composition of the present invention to an area where such control is desired.

As used in this specification and, unless otherwise indicated, the term "herbicide" refers to a molecule or combination of molecules that inhibits or otherwise kills unwanted plants, such as, but not limited to, deleterious or annoying weeds, broadleaf plants, grasses and sedges and can be used for crop protection, edifice protection or turf protection. The term "herbicidally effective amount" means an amount necessary to produce an observable herbicidal effect on unwanted plant growth, including the effects of necrosis, death, growth inhibition, reproduction inhibition, inhibition of proliferation, and removal, destruction, or otherwise diminishing the occurrence and activity of unwanted plants.

The terms "ambient temperature" and "room temperature" as utilized herein shall generally mean any suitable temperature found in a laboratory or other working quarter, and is generally neither below about 15° C. nor above about 30° C.

As used herein, "% by weight of components in the total composition" includes the wt % of all liquid and solid components in the composition.

The process and compositions of the present invention are further illustrated by the examples below. The examples serve only to illustrate the invention and should not be interpreted as limiting since further modifications of the disclosed invention will be apparent to those skilled in the art. All such modifications are deemed to be within the scope of the invention as defined in the claims.

EXAMPLE 1

Preparation of a Suspension Concentrate Formulation of Sulfentrazone and Glyphosate IPA A mixture of 222.3 grams of crystalline sulfentrazone (92.2% purity, milled to less than 10 microns), 2395.5 grams of a 62% aqueous glyphosate IPA solution, 35.7 grams of an alkyl poylglycoside surfactant (AGNIQUE® PG 8105), 35.7 gram of an amine alkylbenzenesulfonic acid surfactant (NI-NATE® 411) in 310.8 grams of water was milled in a Szegvari Attritor system, Type 01STD, for approximately 5 minutes until a uniform mixture was obtained. The mixture was filtered to remove the milling media. To the filtrate, weighing 2,992 grams, was added 245 grams of an aqueous mixture containing 2% xanthan gum (KELZAN® S) and 0.5% anti-microbial agent (LEGEND® MK). This mixture was stirred until homogenous. To a portion of this filtrate, 800.4 grams, was added 25.0 grams of a methyl oleoyl taurate salt (GEROPON® T-77) and 8.3 grams of water. The resultant composition was stirred until a uniform mixture was obtained. The resultant suspension concentrate composition was evenly distributed into six glass jars, sealed and stored for stability testing either at room temperature for initial, one month, three months and 6 months or at 54° C. for two weeks.

At each of the stability test times a sample was evaluated for stability by visual inspection of the suspension concentrate composition for phase separation and sedimentation. Sedimentation in all cases was negligible. In the event that phase separation or sedimentation was observed, the sample was reconstituted to a homogeneous mixture after pouring the sample out of the jar it was stored in into a beaker and back (pour out), recording the number of pour outs needed for reconstitution.

A dilution stability study was conducted at each time station using 2.0 grams of the suspension concentrate composition added to 100.0 mL of water with either 20 ppm or 342 ppm hardness in a 100 mL Nessler tube. The Nessler tube was sealed with a rubber stopper and the contents mixed by inverting the tube ten times. The test samples so produced were maintained at ambient temperature. Re-suspension assessment of the formulation was preformed at 1 hour and at 24 hours and the number of inversions needed to produce a homogenous mixture was recorded. Table 1 below summarizes the stability data.

TABLE 1

Stability Data From Example 1

| | | Stability Time Station and Conditions | | | |
|---|---|---|---|---|---|
| | Initial | 2 Weeks at 54° C. | 1 Month at Room Temperature | 3 Months at Room Temperature | 6 Months at Room Temperature |
| Separation of Phases | zero % | Slight internal phase separation visible | Slight internal phase separation visible | Slight internal phase separation visible | Slight internal phase separation visible |
| Pour Outs | zero | 2 | 3 | 2 | 2 |
| Dilution Stability- number of inversions for re- suspension | | | | | |
| 20 ppm 1 hour | 3 | 3 | 3 | 3 | 3 |
| 20 ppm 24 hours | 5 | 4 | 4 | 6 | 5 |
| 342 ppm 1 hour | 3 | 2 | 3 | 3 | 3 |
| 342 ppm 24 hours | 4 | 3 | 4 | 5 | 5 |

EXAMPLE 2

Suspension Concentrate Formulation of Sulfentrazone and Glyphosate IPA

A mixture of 62.6 pounds of crystalline sulfentrazone (92.2% purity, milled to less than 10 microns), 669.0 pounds of a 62% aqueous glyphosate IPA solution, 2.2 pounds xanthan gum (KELZAN® S), 1.5 pounds of an antimicrobial agent (KATHON™ GC/ICP), 8.0 pounds of an alkyl poylglycoside surfactant (AGNIQUE® PG 8105), 7.0 pounds of an amine alkylbenzenesulfonic acid surfactant (NINATE® 411) and 27.0 pounds of a methyl oleoyl taurate salt (GEROPON® T-77) in 221.8 pounds of water was milled in a media mill, maintaining a temperature of about 25° C., until a particle size distribution where 90% of the particles were between 5 microns and 10 microns was obtained. The milled composition was filtered to remove the beads, and the resultant suspension concentrate was stored in sealed containers for stability testing. Samples were stored for initial, one month, three months and 6 months at room temperature, at 54° C. for two weeks, at 50° C. for 6 months or frozen for two days then thawed at room temperature for one day (freeze/thaw).

At each of the stability test times a sample was evaluated for stability by visual inspection of the suspension concentrate composition for phase separation and sedimentation. In the event that phase separation or sedimentation was observed, the sample was reconstituted to a homogeneous mixture after pouring the sample out of the jar it was stored in into a beaker and back (pour out), recording the number of pour outs needed for reconstitution.

Suspensibility tests were conducted at certain time stations using CIPAC test MT 161, Suspensibility Of Aqueous Suspension Concentrates, CIPAC Handbook, Volume F, 1995 as a guide in either 20 ppm or 342 ppm hardness water.

An assay of the active ingredients by HPLC and particle size analysis was conducted for some stability samples. Table 2 below summarizes the stability data.

TABLE 2

Stability Data From Example 2

Stability Time Station and Conditions

| | Initial | 2 Weeks at 54° C. | 1 Month at 50° C. | Freeze/Thaw Cycle | 3 Months at Room Temperature | 6 Months at Room Temperature |
|---|---|---|---|---|---|---|
| Separation of Phases | zero % | zero % | zero % | zero % | zero % | zero % |
| Suspensibility in Water | | | | | | |
| 20 ppm 2° C. | 100% | 100% | 100% | 100% | — | — |
| 20 ppm 30° C. | 100% | 100% | 100% | 100% | — | — |
| 342 ppm 2° C. | 100% | 100% | 100% | 100% | — | — |
| 342 ppm 30° C. | 100% | 100% | 100% | 100% | — | — |
| Active ingredient assay (HPLC) | | | | | | |
| Sulfentrazone theory = 5.8% | 5.7% | 5.7% | 5.7% | — | 5.8% | 5.7% |
| Glyphosate as the acid theory = 30.8% | 30.4% | 30.0% | 30.0% | — | 29.7% | 30.0% |

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed is:

1. A suspension concentrate composition containing no volatile organic compounds comprising:
   i) crystalline sulfentrazone;
   ii) an aqueous glyphosate salt phase; and
   iii) a surfactant component comprising:
      an amine salt of alkylbenzenesulfonic acid,
      a methyl oleoyl taurate salt, and
      an alkyl polyglycoside.

2. The suspension concentrate composition of claim 1 further comprising one or more of an antifoam agent, an antifreeze agent, a preservative, a thickener or suspending agent and water.

3. The composition of claim 1 wherein the ratio of sulfentrazone to glyphosate salt is from 1:5 to 1:20.

4. The composition of claim 3 in which the ratio of sulfentrazone to glyphosate salt is 1:7.

5. The composition of claim 1 wherein the glyphosate salt is the isopropylamine salt of glyphosate.

6. The composition of claim 1 wherein sulfentrazone is present in an amount from 5% to 7% by weight of all the components in the total composition and the aqueous glyphosate salt phase is present in an amount of 40% to 50% by weight of all the components in the total composition.

7. The composition of claim 6 in which the aqueous glyphosate salt phase is a 62% aqueous solution of the isopropylamine salt of glyphosate.

8. The composition of claim 1 wherein the amine salt of alkylbenzenesulfonic acid is present in an amount of from 0.7% to 1% by weight of all the components in the total composition, the methyl oleoyl taurate salt is present in amount of from 2.7% to 3.0% by weight of all the components in the total composition and the alkyl polyglycoside is present in an amount of from 0.8% to 1% by weight of all of the components in the total composition.

9. A suspension concentrate composition containing no volatile organic compounds comprising:
   i) crystalline sulfentrazone present in an amount of from 5% to 7% by weight of all the components in the total composition;
   ii) an aqueous glyphosate salt phase, comprising a 62% aqueous solution of the isopropylamine salt of glyphosate, present in an amount of 40% to 50% by weight of all the components in the total composition; and iii) a surfactant component comprising:

an amine salt of alkylbenzenesulfonic acid present in an amount of from 0.7% to 1% by weight of all the components in the total composition, a methyl oleoyl taurate salt present in amount of from 2.7% to 3.0% by weight of all the components in the total composition, and an alkyl polyglycoside present in an amount of from 0.8% to 1% by weight of all of the components in the total composition.

10. The composition of claim 9 further comprising one or more of an antifoam agent, an antifreeze agent, a preservative, a thickener or suspending agent and water.

* * * * *